United States Patent [19]

Hagen et al.

[11] Patent Number: 4,589,910
[45] Date of Patent: May 20, 1986

[54] NOVEL 4'(BENZISOTHIAZO-5-YLOXY)-PHENYLUREA DERIVATIVES, THEIR PREPARATION AND THEIR USE AS HERBICIDES

[75] Inventors: Helmut Hagen, Frankenthal; Hans Ziegler, Mutterstadt; Bruno Wuerzer, Otterstadt, all of Fed. Rep. of Germany

[73] Assignee: BASF Aktiengesellschaft, Fed. Rep. of Germany

[21] Appl. No.: 727,628

[22] Filed: Apr. 30, 1985

Related U.S. Application Data

[63] Continuation of Ser. No. 504,604, Jun. 15, 1983, abandoned.

[30] Foreign Application Priority Data

Jun. 19, 1982 [DE] Fed. Rep. of Germany ....... 3222974

[51] Int. Cl.$^4$ ............... C07D 275/04; A01N 47/38
[52] U.S. Cl. ........................... 71/90; 548/207; 544/135; 544/368; 546/202
[58] Field of Search ............... 548/209; 71/88, 241, 71/90; 544/135, 368; 546/202

[56] References Cited

U.S. PATENT DOCUMENTS

| | | | |
|---|---|---|---|
| 2,655,446 | 10/1953 | Todd | 71/120 |
| 2,655,447 | 10/1953 | Todd | 71/120 |
| 3,119,682 | 1/1964 | Martin et al. | 71/90 |
| 3,707,364 | 12/1972 | Becke et al. | 548/207 |
| 3,779,738 | 12/1973 | Pillon et al. | 71/120 |
| 3,808,262 | 4/1974 | Feeh et al. | 71/120 |
| 3,856,860 | 12/1974 | Maravetz | 71/120 |
| 3,864,395 | 2/1975 | Marton et al. | 71/120 |
| 4,273,574 | 6/1981 | Kilpatrick | 71/90 |
| 4,280,835 | 8/1981 | Ichiki et al. | 71/120 |
| 4,364,769 | 12/1982 | Pissiotas et al. | 71/90 |

FOREIGN PATENT DOCUMENTS

| | | | |
|---|---|---|---|
| 623440 | 10/1962 | Belgium . | |
| 36390 | 3/1981 | European Pat. Off. . | |
| 913383 | 12/1962 | United Kingdom | 514/598 |
| 1260386 | 1/1972 | United Kingdom | 514/585 |

*Primary Examiner*—Donald G. Daus
*Assistant Examiner*—G. Hendricks
*Attorney, Agent, or Firm*—Keil & Weinkauf

[57] ABSTRACT

A 4'-(Benzisothiazol-5-yloxy)-phenylureas of the formula

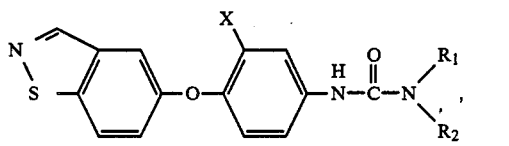

where $R^1$ and $R^2$ are each a saturated straight-chain or branched aliphatic radical of 1 to 10 carbon atoms, an unsaturated straight-chain or branched aliphatic radical of 3 to 10 carbon atoms, or an araliphatic or aromatic radical which may be substituted by 1, 2 or 3 $C_1$–$C_4$-alkyl, $C_1$–$C_4$-alkoxy, cyano, halogen, nitro, monofluoromethyl or trifluoromethyl groups, or are each alkoxy of 1 to 6 carbon atoms, $R^2$ may furthermore be hydrogen, or $R^1$ and $R^2$, together with the nitrogen atom, may be members of a 5-membered or 6-membered ring which may contain further nitrogen and/or oxygen atoms as heteroatoms, and X is hydrogen, trifluoromethyl or chlorine, processes for their preparation, and herbicides containing ureas of the formula I as active ingredients.

6 Claims, No Drawings

NOVEL 4'(BENZISOTHIAZO-5-YLOXY)-PHENYLUREA DERIVATIVES, THEIR PREPARATION AND THEIR USE AS HERBICIDES

This application is a continuation of application Ser. No. 504,604, filed on June 15, 1983, now abandoned.

The present invention relates to novel 4'-(benzisothiazol-5-yloxy)-phenylurea derivatives, processes for their preparation and herbicides which contain these compounds as active ingredients.

Naphthyloxy- and phenoxy phenylureas having herbicidal properties have been disclosed (for example, German Laid-Open Application DOS 2,853,791, Belgian Pat. Nos. 593,743 and 623,440, Dutch Laid-Open Application No. 6,901,066, and European Laid-Open Application No. 36,390).

However, the usefulness of a herbicide depends not only on how powerful an action it exhibits, but to a certain extent also on its selectivity with regard to crop plants. Such selectivities require a very specific chemical structure, which cannot be derived by drawing analogies to known structures.

It is an object of the present invention to provide herbicides having more advantageous properties.

We have found that this object is achieved by the 4'-(benzisothiazol-5-yloxy)-phenylureas as claimed in claim 1.

We have found that 4'-(benzisothiazol-5-yloxy)-phenylureas of the formula I

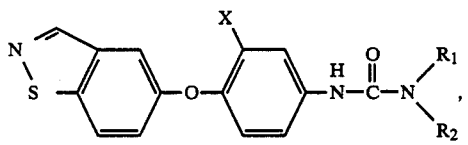

where $R^1$ and $R^2$ are each a saturated straight-chain or branched aliphatic radical of 1 to 10 carbon atoms, an unsaturated straight-chain or branched aliphatic radical of 3 to 10 carbon atoms, or an araliphatic or aromatic radical which may be substituted by 1, 2 or 3 $C_1$-$C_4$-alkyl, $C_1$-$C_4$-alkoxy, cyano, halogen, nitro, monofluoromethyl or trifluoromethyl groups, or are each alkoxy of 1 to 6 carbon atoms, $R^2$ may furthermore be hydrogen, or $R^1$ and $R^2$, together with the nitrogen atom, may be members of a 5-membered or 6-membered ring which may contain further nitrogen and/or oxygen atoms as heteroatoms, and X is hydrogen, trifluoromethyl or chlorine, have a selective herbicidal action when used for controlling undesirable plant growth in crop plants. The novel compounds can be prepared by the following methods:

(a) A 5-(4'-aminophenoxy)-benzisothiazole of the formula II

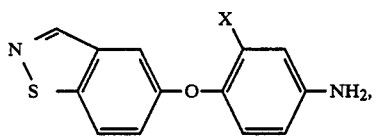

where X has the above meanings, is reacted with an isocyanate of the formula III

where $R^1$ has the above meanings, in an inert diluent and in the presence of a catalyst.

The reaction can be represented by the following equation:

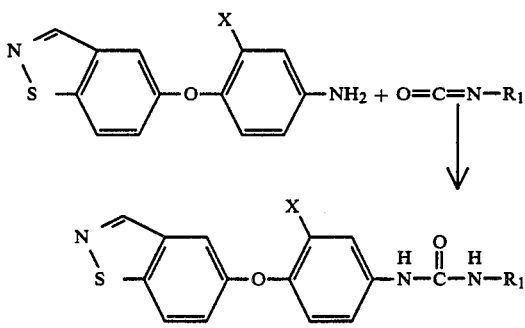

Suitable inert solvents for the reaction are aliphatic or aromatic hydrocarbons, e.g. gasoline, benzene or toluene, carboxylic acid nitriles, e.g. acetonitrile, ketones, e.g. acetone, chlorohydrocarbons, e.g. dichloromethane, chloroform or tetrachloromethane, and ethers and cyclic ethers, e.g. diethyl ether, diisopropyl ether, tetrahydrofuran or dioxane, preferred solvents being toluene and dioxane. The catalyst added is an inert base, and this is employed in an amount of from 1 to 0.001, preferably from 0.02 to 0.05, part per part of starting material of the formula II. Triethylamine is the preferred base.

The reaction is carried out at from 0° to 200° C., preferably from 60° to 100° C.

Compounds of the formula I in which $R^2$ is hydrogen are obtainable by the reaction.

(b) A 5-(4'-isocyanatophenoxy)-benzisothiazole of the formula IV

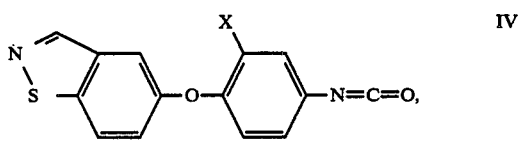

where X has the above meanings, is reacted with an amine of the formula V

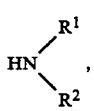

where $R^1$ and $R^2$ have the above meanings, in an inert solvent.

The reaction can be represented by the following equation:

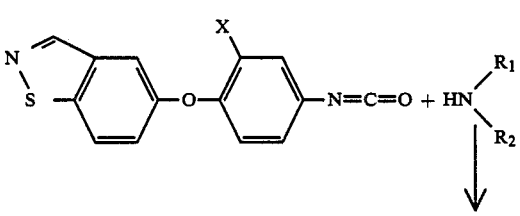

-continued

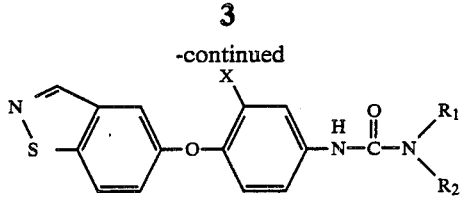

The inert solvents which can be used for the synthesis described under (a) are also suitable for this reaction, but in this case acetonitrile and ethers, e.g. diethyl ether, tetrahydrofuran and dioxane, are preferred.

The reaction is carried out at from −70° to 150° C., preferably from 0° to 30° C.

In the compounds of the formula I, $R^1$ and $R^2$ preferably have the following meanings:

(a) where X is hydrogen or chlorine, $R^1$ and $R^2$ are each methyl or $R^1$ is methyl and $R^2$ is methoxy;

(b) where X is trifluoromethyl, $R^1$ is methyl and $R^2$ is hydrogen, or $R^1$ is methyl and $R^2$ is 1-methylpropynyl, or $R^1$ and $R^2$, together with the nitrogen atom, form a morpholin-4-yl radical.

PREPARATION

The Examples which follow illustrate the preparation of the starting materials. Parts are by weight.

Starting material 1

5-(4'-Aminophenoxy)-benzisothiazole

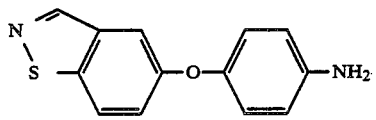

A solution of 56 parts of potassium hydroxide in 30 parts of water was added to a solution of 151 parts of 5-hydroxybenzisothiazole in 500 parts of methanol at from 20° to 30° C., the solution was evaporated to dryness under reduced pressure, and the residue was dissolved in 850 parts of dimethylsulfoxide. 141 parts of 1-fluoro-4-nitrobenzene were added to this solution, the reaction mixture was stirred for 12 hours at 80° C., 1,000 parts of water were added and the mixture was then extracted with dichloromethane. 226 parts (83% of theory) of 5-(4'-nitrophenoxy)-benzisothiazole of melting point 103° C. were obtained.

109 parts of this product in 600 parts of ethanol were shaken with 3 parts of a palladium/active carbon catalyst in the presence of hydrogen at 50° C. in a hydrogenation apparatus until hydrogen was no longer absorbed. The catalyst was removed, and the mixture was evaporated down to give 85 parts (88% of theory) of 5-(4'-aminophenoxy)-benzisothiazole of melting point 100° C.

Starting material 2

5-(4'-Isocyanatophenoxy)-benzisothiazole

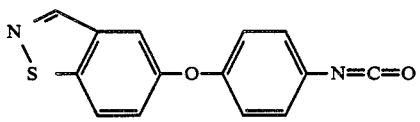

58 parts of phosgene were passed into a solution of 60.5 parts of 5-(4'-aminophenoxy)-benzisothiazole in 400 parts of chlorobenzene at from −5° to −10° C., the reaction mixture was stirred for 1 hour at from 20° to 30° C. and then slowly brought to 100° C., and the solvent and excess phosgene were removed under reduced pressure to give 65 parts (97% of theory) of 5-(4'-isocyanatophenoxy)-benzisothiazole as a pale oil, which was used directly for the preparation of the compounds of the formula I.

Starting material 3

5-(4'-Amino-2'-chlorophenoxy)-benzisothiazole

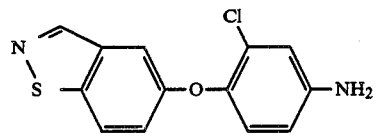

151 parts of 5-hydroxybenzisothiazole were reacted with 192 parts of 3,4-dichloronitrobenzene by a procedure similar to that described for starting material 1. 240 parts (78% of theory) of 5-(2'-chloro-4'-nitrophenoxy)-benzisothiazole of melting point 150° C. were obtained.

61.3 parts of this product were reduced by a procedure similar to that described for starting material 1. 55 parts (99% of theory) of 5-(4'-amino-2'-chlorophenoxy)-benzisothiazole were obtained.

Starting material 4

5-(2'-Chloro-4'-isocyanatophenoxy)-benzisothiazole

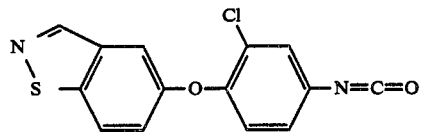

55.3 parts of 5-(4'-amino-2'-chlorophenoxy)-benzisothiazole were reacted with phosgene by a procedure similar to that described for starting material 2. 60 parts (99% of theory) of 5-(2'-chloro-4'-isocyanatophenoxy)-benzisothiazole were obtained as a pale oil.

Starting material 5

5-(4'-Amino-2'-trifluoromethylphenoxy)-benzisothiazole

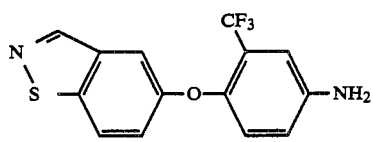

120 parts of 5-hydroxybenzisothiazole were reacted with 176 parts of 2-chloro-5-nitrobenzotrifluoride by a procedure similar to that described for starting material 1. 253 parts (93% of theory) of 5-(4'-nitro-2'-trifluoromethylphenoxy)-benzisothiazole of melting point 124° C. were obtained.

136 parts of this product were reduced with hydrogen by a procedure similar to that described for starting material 2. 110 parts (89% of theory) of 5-(4'-amino-2'-trifluoromethylphenoxy)-benzisothiazole of melting point 136° C. were obtained.

Starting material 6

5-(4′-Isocyanato-2′-trifluoromethylphenoxy)-benzisothiazole

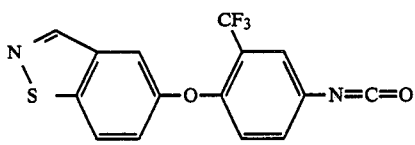

124 parts of 5-(4′-amino-2′-trifluoromethylphenoxy)-benzisothiazole were reacted with 70 parts of phosgene by a procedure similar to that described for starting material 2. 130 parts (97% of theory) of 5-(4′-isocyanato-2′-trifluoromethylphenoxy)-benzisothiazole were obtained as a pale oil.

EXAMPLE 1

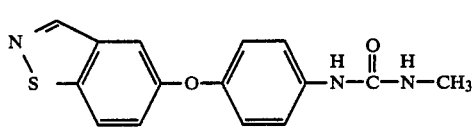

5-(4′-Methylaminocarbonylaminophenoxy)-benzisothiazole 24.2 parts of 5-(4′-aminophenoxy)-benzisothiazole, 400 parts of toluene, 1 part of triethylamine and 11.4 parts of methyl isocyanate were heated at 80° C. for 12 hours, and the reaction mixture was then evaporated down under reduced pressure. 25 parts (85% of theory) of 5-(4′-methylaminocarbonylaminophenoxy)-benzisothiazole of melting point 178° C. were obtained.

EXAMPLE 2

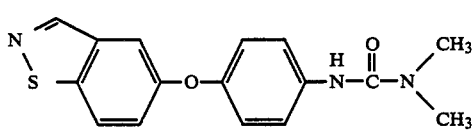

5-(4′-Dimethylaminocarbonylaminophenoxy)-benzisothiazole 5 parts of gaseous dimethylamine were passed into a solution of 26.8 parts of 5-(4′-isocyanatophenoxy)-benzisothiazole in 300 parts of diethyl ether, the reaction mixture was stirred for 12 hours at from 20 to 30° C., and the resulting precipitate was isolated. 27.6 parts (88% of theory) of 5-(4′-dimethylaminocarbonylaminophenoxy)-benzisothiazole of melting point 156° C. were obtained.

EXAMPLE 3

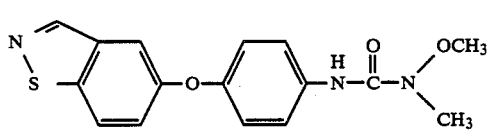

5-(4′-(N-Methoxy-N-methylaminocarbonylamino)-phenoxy)-benzisothiazole 6.1 parts of N-methoxy-N-methylamine were added to a solution of 26.8 parts of 5-(4′-isocyanatophenoxy)-benzisothiazole in 300 parts of diethyl ether at from 20° to 30° C., the mixture was stirred for 12 hours at this temperature and then evaporated down, and the residue was triturated in about 50 parts of diethyl ether, isolated and dried. 26 g (82% of theory) of 5-(4′-(N-methoxy-N-methylaminocarbonylamino)-phenoxy)-benzisothiazole of melting point 108° C. were obtained.

The compounds of Examples 4 to 10 were prepared by a procedure similar to that of Example 2.

EXAMPLE 4

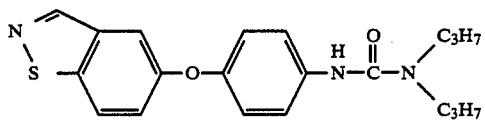

5-(4′-Dipropylaminocarbonylaminophenoxy)-benzisothiazole: mp. 113° C.

EXAMPLE 5

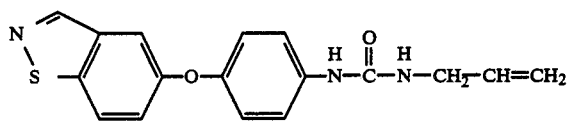

5-(4′-Allylaminocarbonylaminophenoxy)-benzisothiazole: mp. 98° C.

EXAMPLE 6

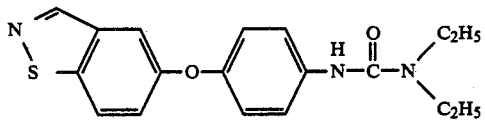

5-(4′-Diethylaminocarbonylaminophenoxy)-benzisothiazole: mp. 147° C.

EXAMPLE 7

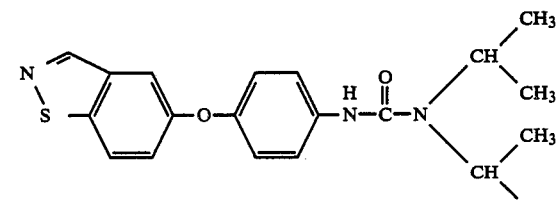

5-(4′-Diisopropylaminocarbonylaminophenoxy)-benzisothiazole: mp. 137° C.

EXAMPLE 8

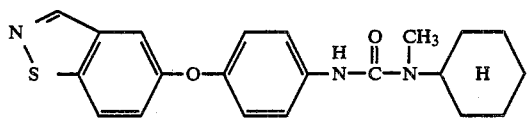

5-(4'-(N-Methyl-N-cyclohexylaminocarbonylamino)-phenoxy)-benzisothiazole.

EXAMPLE 9

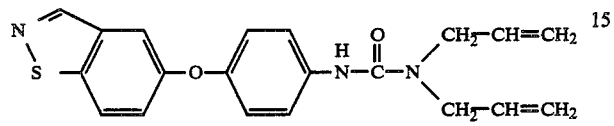

5-(4'-Diallylaminocarbonylaminophenoxy)-benzisothiazole: mp. 113° C.

EXAMPLE 10

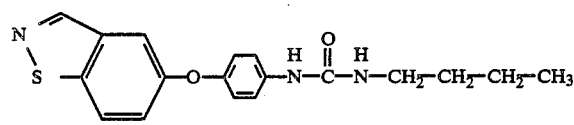

5-(4'-n-Butylaminocarbonylaminophenoxy)-benzisothiazole: mp. 120° C.

EXAMPLE 11

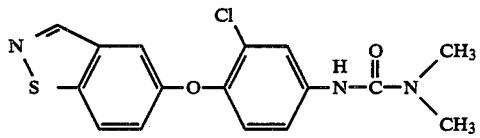

5-(2'-Chloro-4'-dimethylaminocarbonylaminophenoxy)-benzisothiazole 5 parts of gaseous dimethylamine were passed into 30.3 parts of 5-(2'-chloro-4'-isocyanatophenoxy)-benzisothiazole and 300 parts of diethyl ether at from 20° to 30° C., the mixture was stirred for 12 hours at this temperature and the resulting precipitate was then isolated and dried. 27.5 parts (70% of theory) of 5-(2'-chloro-4'-dimethylaminocarbonylaminophenoxy)-benzisothiazole of melting point 149° C. were obtained.

EXAMPLE 12

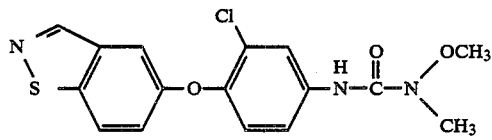

5-[2'-Chloro-4'-(N-methoxy-N-methylaminocarbonylamino)-phenoxy]-benzisothiazole

A solution of 6.1 parts of N-methoxy-N-methylamine in 100 parts of diethyl ether was added to a solution of 30.3 parts of 5-(2'-chloro-4'-isocyanatophenoxy)-benzisothiazole in 300 parts of diethyl ether at from 20° to 30° C., and after 12 hours at this temperature the reaction mixture was evaporated down and the residue was treated with about 50 parts of diethyl ether. 30.2 parts (83% of theory) of 5-[2'-chloro-4'-(N-methoxy-N-methylaminocarbonylamino)-phenoxy]-benzisothiazole of melting point 128° C. were obtained.

EXAMPLE 13

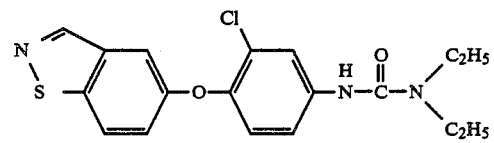

5-(2'-Chloro-4'-diethylaminocarbonylaminophenoxy)-benzisothiazole of melting point 141° C. was prepared by a procedure similar to that of Example 12.

EXAMPLE 14

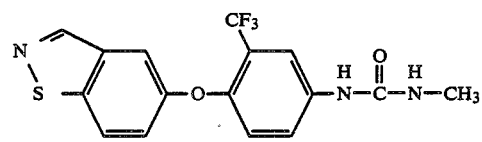

5-(4'-Methylaminocarbonylamino-2'-trifluoromethylphenoxy)-benzisothiazole 31 parts of 5-(4'-amino-2'-trifluoromethylphenoxy)-benzisothiazole, 400 parts of toluene, 1 part of triethylamine and 11.4 parts of methyl isocyanate were stirred for 12 hours at 80° C., after which the solvent was removed under reduced pressure and the residue was purified over silica gel, using chloroform as the mobile phase. 29.4 parts (80% of theory) of 5-(4'-methylaminocarbonylamino-2'-trifluoromethylphenoxy)-benzisothiazole of melting point 138° C. were obtained.

EXAMPLE 15

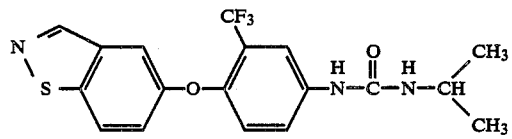

5-(4'-Isopropylaminocarbonylamino-2'-trifluoromethylphenoxy)-benzisothiazole of melting point 158° C. was prepared by a procedure similar to that of Example 14.

EXAMPLE 16

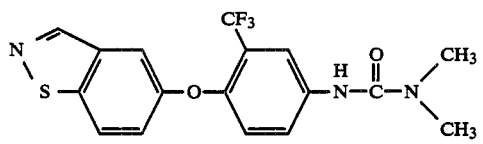

5-(4'-Dimethylaminocarbonylamino-2'-trifluoromethylphenoxy)-benzisothiazole 5 parts of gaseous dimethylamine were passed into a solution of 33.6 parts of 5-(4'-isocyanato-2'-trifluoromethylphenoxy)-benzisothiazole in 400 parts of acetonitrile at from 10° to 20° C. and the reaction was allowed to continue for 12 hours at from 20° to 30° C., after which the solvent was removed under reduced pressure and the residue was recrystallized from chloroform. 32.7 parts (86% of theory) of 5-(4'-dimethylaminocarbonylamino-2'-trifluoromethylphenoxy)-benzisothiazole of melting point 188° C. were obtained.

EXAMPLE 17

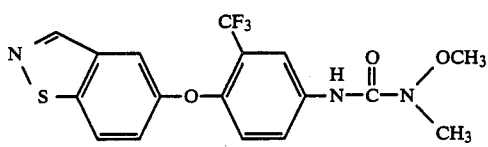

5-[4'-(N-Methoxy-N-methylaminocarbonylamino)-2'-trifluoromethylphenoxy]-benzisothiazole A solution of 6.1 parts of N-methoxy-N-methylamine in 100 parts of diethyl ether was added to a solution of 33.6 parts of 5-(4'-isocyanato-2'-trifluoromethylphenoxy)-benzisothiazole in 300 parts of diethyl ether at from 20 to 30° C., the reaction mixture was stirred for 12 hours at this temperature and the resulting precipitate was then isolated. 33 parts (83% of theory) of 5-[4'-(N-methoxy-N-methylaminocarbonylamino)-2'-trifluoromethylphenoxy]-benzisothiazole of melting point 197° C. were obtained.

The compounds of Examples 18 to 24 were prepared by a procedure similar to that of Example 17.

EXAMPLE 18

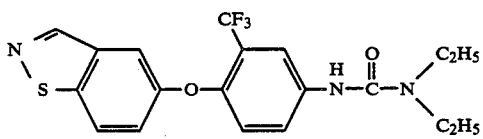

5-(4'-Diethylaminocarbonylamino-2'-trifluoromethylphenoxy)-benzisothiazole: mp. 156° C.

EXAMPLE 19

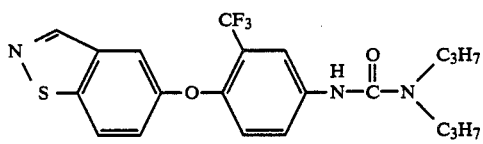

5-[4'-n-Dipropylaminocarbonylamino-2'-trifluoromethylphenoxy]-benzisothiazole: mp. 129° C.

EXAMPLE 20

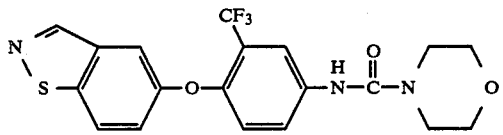

5-[4'-(Morpholin-4''-ylcarbonylamino)-2'-trifluoromethylphenoxy]-benzisothiazole: oil.

EXAMPLE 21

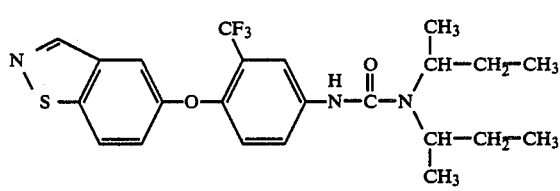

5-[4'-(Di-sec.butylaminocarbonylamino)-2'-trifluoromethylphenoxyl[-benzisothiazole: mp. 100° C.

EXAMPLE 22

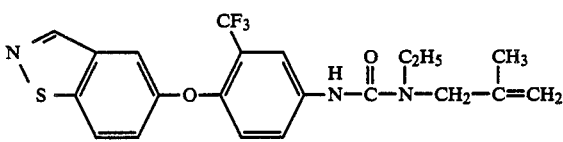

5-[4'-(N-Ethyl-N-methallylaminocarbonylamino)-2'-trifluoromethylphenoxy[-benzisothiazole: oil.

EXAMPLE 23

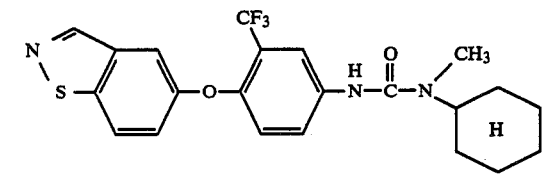

5-[4'-(N-Methyl-N-cyclohexylaminocarbonylamino-2'-trifluoromethylphenoxy[-benzisothiazole: mp. 147° C.

EXAMPLE 24

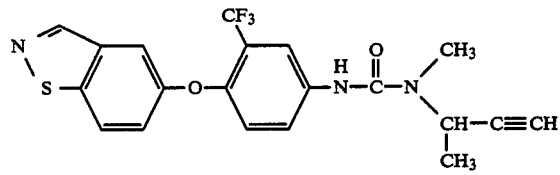

5[4'-(N-Methyl-N-1-methylpropyn-1-ylaminocarbonylamino)-2'-trifluoromethylphenoxy]-benzisothiazole: oil.

Application

The active ingredients may be applied for instance in the form of directly sprayable solutions, powders, suspensions (including high-percentage aqueous, oily or other suspensions), dispersions, emulsions, oil dispersions, pastes, dusts, broadcasting agents, or granules by spraying, atomizing, dusting, broadcasting or watering. The forms of application depend entirely on the purpose for which the agents are being used.

For the preparation of solutions, emulsions, pastes and oil dispersions to be sprayed direct, mineral oil fractions of medium to high boiling point, such as kerosene or diesel oil, further coal-tar oils, and oils of vegetable or animal origin, aliphatic, cyclic and aromatic hydrocarbons such as benzene, toluene, xylene, paraffin, tetrahydronaphthalene, alkylated naphthalenes and their derivatives such as methanol, ethanol, propanol, butanol, chloroform, carbon tetrachloride, cyclohexanol, cyclohexanone, chlorobenzene, isophorone, etc., and strongly polar solvents such as dimethylformamide, dimethyl sulfoxide, N-methylpyrrolidone, water, etc. are suitable.

Aqueous formulations may be prepared from emulsion concentrates, pastes, oil dispersions or wettable powders by adding water. To prepare emulsions, pastes and oil dispersions the ingredients as such or dissolved in an oil or solvent may be homogenized in water by means of wetting or dispersing agents, adherents or emulsifiers. Concentrates which are suitable for dilution with water may be prepared from active ingredient, wetting agent, adherent, emulsifying or dispersing agent and possibly solvent or oil.

Examples of surfactants are: alkali metal, alkaline earth metal and ammonium salts of ligninsulfonic acid, naphthalenesulfonic acids, phenolsulfonic acids, alkylaryl sulfonates, alkyl sulfates, and alkyl sulfonates, alkali metal and alkaline earth metal salts of dibutylnaphthalenesulfonic acid, lauryl ether sulfate, fatty alcohol sulfates, alkali metal and alkaline earth metal salts of fatty acids, salts of sulfated hexadecanols, heptadecanols, and octadecanols, salts of sulfated fatty alcohol glycol ethers, condensation products of sulfonated naphthalene and naphthalene derivatives with formaldehyde, condensation products of naphthalene or naphthalenesulfonic acids with phenol and formaldehyde, polyoxyethylene octylphenol ethers, ethoxylated isooctylphenol, ethoxylated octylphenol and ethoxylated nonylphenol, alkylphenol polyglycol ethers, tributylphenyl polyglycol ethers, alkylaryl polyether alcohols, isotridecyl alcohol, fatty alcohol ethylene oxide condensates, ethoxylated castor oil, polyoxyethylene alkyl ethers, ethoxylated polyoxypropylene, lauryl alcohol polyglycol ether acetal, sorbitol esters, lignin, sulfite waste liquors and methyl cellulose.

Powders, dusts and broadcasting agents may be prepared by mixing or grinding the active ingredients with a solid carrier.

Granules, e.g., coated, impregnated or homogeneous granules, may be prepared by bonding the active ingredients to solid carriers. Examples of solid carriers are mineral earths such as silicic acid, silica gels, silicates, talc, kaolin, Attaclay, limestone, lime, chalk, bole, loess, clay, dolomite, diatomaceous earth, calcium sulfate, magnesium sulfate, magnesium oxide, ground plastics, fertilizers such as ammonium sulfate, ammonium phosphate, ammonium nitrate, and ureas, and vegetable products such as grain flours, bark meal, wood meal, and nutshell meal, cellulosic powders, etc.

The formulations contain from 0.1 to 95, and preferably 0.5 to 90, % by weight of active ingredient. Application rates are from 0.1 to 10 kg of active ingredient per hectare.

The active ingredients are applied to the plants or soil for instance by watering, broadcasting, dusting, spraying or atomizing, by coating the plants with them, or by introducing them into the irrigation water.

The agents may be applied pre or postemergence. Preferably, the novel active ingredients are applied after emergence of the unwanted plants. If certain crop plants tolerate the active ingredients less well, application techniques may be used in which the the herbicidal agents are sprayed from suitable equipment in such a manner that the leaves of sensitive crop plants are if possible not touched, and the agents reach the soil or the unwanted plants growing beneath the crop plants (post-directed, lay-by treatment).

The amount of active ingredient applied depends on the time of the year, the objective to be achieved, the plants to be combated and the growth stage of the plants, and varies from 0.1 to 5 kg/ha.

The influence of representatives of the novel 5-phenoxybenzisothiazole-4'-urea derivatives on the growth of unwanted und crop plants is demonstrated in greenhouse experiments.

The vessels employed were plastic flowerpots having a volume of 300 cm$^3$, and which were filled with a sandy loam containing about 1.5% humus. For the postemergence treatment, described here, the plants were first grown in the vessels to a height of from 3 to 15 cm, depending on growth form, before being treated. The soybean plants were grown in a peat-enriched substrate to ensure better growth than is possible in a sandy loam. For this treatment, either plants which had been sown directly in the pots and grown there were selected, or plants which had been grown separately as seedlings and transplanted to the experiment vessels a few days before treatment. The agents were suspended or emulsified in water as vehicle and sprayed through finely distributing nozzles. The application rates varied from ingredient to ingredient, and were 0.5, 2.0 and 3.0 kg of active ingredient per hectare.

The following test plants were used for the experiments:

| Botanical name | Common name |
|---|---|
| Amaranthus spp. | pigweed |
| Avena sativa | oats |
| Cassia tora | sicklepod |
| Centaurea cyanus | cornflower |
| Chenopodium album | lambsquarters |
| Glycine max. | soybeans |
| Ipomoea spp. | morningglory |
| Sinapis alba | white mustard |
| Triticum aestivum | wheat |

The pots were set up in the greenhouse—species from warmer areas at from 20° to 35° C., and species from moderate climates at 15° to 20° C. The experiments were run for 2–4 weeks. During this period, the plants were tended and their reactions to the various treatments assessed. The scale used for assessment was 0 to 100, 0 denoting no damage or normal emergence, and 100 denoting nonemergence or complete destruction of at least the visible plant parts.

The greenhouse experiments demonstrate the herbicidal action of compounds nos. 2, 3 and 14 (prepared in accordance with Examples 2, 3 and 14) on postemergence application of 3.0 kg/ha. They also reveal a herbicidal action for example for compounds nos. 20 and 24 on postemergence application of 2.0 kg/ha.

Compound no. 14 has a selective herbicidal action in soybeans and wheat on postemergence application of 0.5 kg/ha, and compound no. 11 has a selective herbicidal action in oats on postemergence application of 3.0 kg/ha.

In view of the good tolerance by numerous broad-leaved and other crops, and the many application methods possible, the herbicides according to the invention, or agents containing them, may be used in a large number of crop plants for removing unwanted plant growth.

The following crop plants may be mentioned by way of example:

| Botanical name | Common name |
| --- | --- |
| Allium cepa | onions |
| Ananas comosus | pineapples |
| Arachis hypogaea | peanuts (groundnuts) |
| Asparagus officinalis | asparagus |
| Avena sativa | oats |
| Beta vulgaris spp. altissima | sugarbeets |
| Beta vulgaris spp. rapa | fodder beets |
| Beta vulgaris spp. esculenta | table beets, red beets |
| Brassica napus var. napus | rape seed |
| Brassica napus var. napobrassica | |
| Brassica napus var. rapa | turnips |
| Brassica rapa var. silvestris | |
| Camellia sinensis | tea plants |
| Carthamus tinctorius | safflower |
| Carya illinoinensis | pecan trees |
| Citrus limon | lemons |
| Citrus maxima | grapefruits |
| Citrus reticulata | mandarins |
| Citrus sinensis | orange trees |
| Coffea arabica (Coffea canephora, Coffea liberica) | coffee plants |
| Cucumis melo | melons |
| Cucumis sativus | cucumbers |
| Cynodon dactylon | Bermudagrass in turf and lawns |
| Daucus carota | carrots |
| Elais guineensis | oil palms |
| Fragaria vesca | strawberries |
| Glycine max | soybeans |
| Gossypium hirsutum (Gossypium arboreum Gossypium herbaceum Gossypium vitifolium) | cotton |
| Helianthus annuus | sunflowers |
| Helianthus tuberosus | |
| Hevea brasiliensis | rubber plants |
| Hordeum vulgare | barley |
| Humulus lupulus | hops |
| Ipomoea batatas | sweet potatoes |
| Juglans regia | walnut trees |
| Lactuca sativa | lettuce |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Mentha piperita | peppermint |
| Musa spp. | banana plants |
| Nicothiana tabacum (N. rustica) | tobacco |
| Olea europaea | olive trees |
| Oryza sativa | rice |
| Panicum miliaceum | |
| Phaseolus lunatus | limabeans |
| Phaseolus mungo | mungbeans |
| Phaseolus vulgaris | snapbeans, green beans, dry beans |
| Pennisetum glaucum | |
| Petroselinum crispum spp. tuberosum | parsley |
| Picea abies | Norway spruce |
| Abies alba | fir trees |
| Pinus spp. | pine trees |
| Pisum sativum | English peas |
| Prunus avium | cherry trees |
| Prunus domestica | plum trees |
| Prunus dulcis | almond trees |
| Prunus persica | peach trees |
| Pyrus communis | pear trees |
| Ribes sylvestre | redcurrants |
| Ribes uva-crispa | gooseberries |
| Ricinus communis | castor-oil plants |
| Saccharum officinarum | sugar cane |
| Secale cereale | rye |
| Sesamum indicum | sesame |
| Solanum tuberosum | Irish potatoes |
| Sorghum bicolor (s. vulgare) | sorghum |
| Sorghum dochna | |
| Spinacia oleracea | spinach |
| Theobroma cacao | cacao plants |
| Trifolium pratense | red clover |
| Triticum aestivum | wheat |
| Vaccinium corymbosum | blueberries |
| Vaccinium vitis-idaea | cranberries |
| Vicia faba | tick beans |
| Vigna sinensis (V. unguiculata) | cow peas |
| Vitis vinifera | grapes |
| Zea mays | Indian corn, sweet corn, maize |

To increase the spectrum of action and to achieve synergistic effects, the novel compounds may be mixed and applied together with numerous other herbicidal active ingredients. Examples of suitable mixture components are diazines, 4H-3,1-benzoxazine derivatives, benzothiadiazinones, 2,6-dinitroanilines, N-phenylcarbamates, thiolcarbamates, halocarboxylic acids, triazines, amides, ureas, diphenyl ethers, triazinones, uracils, benzofuran derivatives, cyclohexane-1,3-dione derivatives, etc.

It may also be useful to apply the novel compounds, either alone or in combination with other herbicides, in admixture with other crop protection agents, e.g., agents for combating pests or phytopathogenic fungi or bacteria. The compounds may also be mixed with solutions of mineral salts used to remedy nutritional or trace element deficiencies. Non-phytotoxic oils and oil concentrates may also be added.

TABLE 1

Herbicidal action of compounds according to the invention on postemergence application of 3.0 kg/ha in the greenhouse

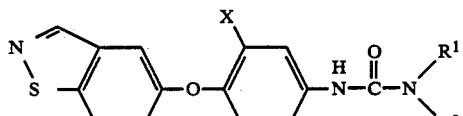

| Compound no. | X | R¹ | R² | Test plants and % damage | | |
| --- | --- | --- | --- | --- | --- | --- |
| | | | | Amaranthus spp. | Ipomoea spp. | Centaurea cyanus |
| 14 | CF₃ | H | CH₃ | 100 | 100 | 90 |
| 3 | H | CH₃ | OCH₃ | 100 | 100 | 100 |
| 2 | H | CH₃ | CH₃ | 100 | 70 | 100 |

TABLE 2

Herbicidal action on postemergence application of 2.0 kg/ha in the greenhouse, with reference to the broadleaved plant *Sinapis alba*

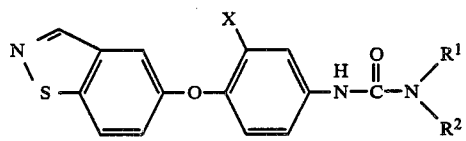

| Compound no. | X | $R^1$ | $R^2$ | Damage in % |
|---|---|---|---|---|
| 20 | $CF_3$ | | (morpholino) | 90 |
| 24 | $CF_3$ | $-CH_3$ | $-CH(CH_3)-C{\equiv}CH$ | 95 |

TABLE 3

Selective control of *Chenopodium album* on postemergence application of compound no. 14 in the greenhouse

| Test plants | Damage in % at 0.5 kg/ha |
|---|---|
| *Glycine max.* | 5 |
| *Triticum aestivum* | 3 |
| *Chenopodium album* | 90 |

TABLE 4

Selective control of unwanted broadleaved plants in oats with compound no. 11; postemergence application of 3.0 kg/ha in the greenhouse

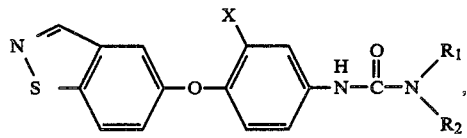

| Test plants | Damage in % |
|---|---|
| *Avena sativa* | 0 |
| *Amaranthus* spp. | 90 |
| *Ipomoea* spp. | 100 |
| *Centaurea cyanus* | 100 |
| *Cassia tora* | 100 |

We claim:

1. A 4'-(benzisothiazol-5-yloxy)-phenylurea of the formula

I where $R^1$ and $R^2$ are each a saturated straight-chain or branched aliphatic radical of 1 to 10 carbon atoms, an unsaturated straight-chain or branched aliphatic radical of 3 to 10 carbon atoms, or an araliphatic or aromatic radical which may be substituted by 1, 2 or 3 $C_1$-$C_4$-alkyl, $C_1$-$C_4$-alkoxy, cyano, halogen, nitro, monofluoromethyl or trifluoromethyl groups, or are each alkoxy of 1 to 6 carbon atoms, $R^2$ may furthermore be hydrogen, or $R^1$ and $R^2$, together with the nitrogen atom, may be members of a 5-membered or 6-membered ring which may contain further nitrogen and/or oxygen atoms as heteroatoms, and X is hydrogen, trifluoromethyl or chlorine.

2. A herbicide containing a solid or liquid carrier and an effective amount of at least one compound of the formula I as defined in claim 1.

3. A compound of the formula I as defined in claim 1, wherein X is hydrogen or chlorine and $R^1$ and $R^2$ are each methyl or $R^1$ is methyl and $R^2$ is methoxy.

4. A compound of the formula I as defined in claim 1, wherein X is trifluoromethyl, $R^1$ is methyl and $R^2$ is hydrogen.

5. A compound of the formula I as defined in claim 1, wherein X is trifluoromethyl, $R^1$ is methyl and $R^2$ is 1-methylpropynyl.

6. A compound of the formula I as defined in claim 1, wherein X is trifluoromethyl and $R^1$ and $R^2$ together with the nitrogen atom form a morpholin-4-yl radical.

* * * * *